United States Patent
Yam et al.

(10) Patent No.: US 9,220,407 B2
(45) Date of Patent: Dec. 29, 2015

(54) DOUBLE FUNCTION TILTING HEAD OPHTHALMIC INSTRUMENT

(75) Inventors: Ran Yam, Jerusalem (IL); Aderet Sompolinsky, Jerusalem (IL); Ian Melnick, Jerusalem (IL)

(73) Assignee: Visionix Ltd., Jerusalem (IL)

( * ) Notice: Subject to any disclaimer, the term of this patent is extended or adjusted under 35 U.S.C. 154(b) by 61 days.

(21) Appl. No.: 14/342,433

(22) PCT Filed: Sep. 6, 2012

(86) PCT No.: PCT/IL2012/000334
§ 371 (c)(1),
(2), (4) Date: Mar. 3, 2014

(87) PCT Pub. No.: WO2013/035091
PCT Pub. Date: Mar. 14, 2013

(65) Prior Publication Data
US 2014/0211161 A1    Jul. 31, 2014

Related U.S. Application Data

(60) Provisional application No. 61/573,120, filed on Sep. 7, 2011.

(51) Int. Cl.
*A61B 3/14* (2006.01)
*A61B 3/00* (2006.01)
(Continued)

(52) U.S. Cl.
CPC . *A61B 3/103* (2013.01); *A61B 3/14* (2013.01); *A61B 3/152* (2013.01); *A61B 3/16* (2013.01); *A61B 3/18* (2013.01)

(58) Field of Classification Search
USPC .................................................. 351/200–246
See application file for complete search history.

(56) References Cited

U.S. PATENT DOCUMENTS 5,512,965 A *  4/1996  Snook .......................... 351/205
6,193,371 B1    2/2001  Snook
(Continued)

FOREIGN PATENT DOCUMENTS

WO    94/02064 A1    2/1994
WO    2009/024981 A2    2/2009

OTHER PUBLICATIONS

Extended Supplementary European Search Report dated Mar. 17, 2015 in corresponding European patent application No. 12830784.0.
(Continued)

*Primary Examiner* — Mohammed Hasan
(74) *Attorney, Agent, or Firm* — Maine Cernota & Rardin

(57) ABSTRACT

Systems for performing sequential multiple function ophthalmic measurements using separate measurement instruments, by mechanical switching between the instruments. In prior art systems, the separate measurement instruments are stacked, and transfer between them is performed by means of a linear mechanical motion stage. The separate measurement instruments of the present application are mounted on a base which is rotatably pivoted around a joint at a location remote from the optical entry apertures of the instruments. The entrance apertures of the measurement instruments then traverse the eye being measured sequentially. A rotational motion around the pivoted joint is thus transformed into a linear motion at the eye of the subject, without the need for a linear motion stage. A Scheimpflug camera corneal thickness measurement is also described, in which the measurement head is tilted during the corneal scan such that the illuminating slit beam always impinges on the cornea normally.

14 Claims, 3 Drawing Sheets

(51) Int. Cl.
*A61B 3/103* (2006.01)
*A61B 3/18* (2006.01)
*A61B 3/16* (2006.01)
*A61B 3/15* (2006.01)

(56) References Cited

U.S. PATENT DOCUMENTS

| | | |
|---|---|---|
| 6,286,958 B1 | 9/2001 | Koest et al. |
| 7,364,298 B2 | 4/2008 | Hayashi et al. |
| 7,515,321 B2 | 4/2009 | Mimura et al. |
| 7,771,050 B2 | 8/2010 | Honda et al. |
| 7,909,462 B2 | 3/2011 | Takahashi et al. |
| 2004/0210106 A1 | 10/2004 | Banju |
| 2007/0097317 A1 | 5/2007 | Hayashi et al. |
| 2011/0032480 A1 | 2/2011 | Rathjen |
| 2011/0299034 A1* | 12/2011 | Walsh et al. .................. 351/206 |

OTHER PUBLICATIONS

PCT International Search Report and Written Opinion of the ISA, mailed Jan. 16, 2013 in PCT/IL2012/000334.

English translation of Office Action dated Sep. 14, 2015 of the Chinese Patent Office, in corresponding CN patent application No. 201280043555.3.

* cited by examiner

DOUBLE FUNCTION TILTING HEAD OPHTHALMIC INSTRUMENT

RELATED APPLICATIONS

This application is a national phase application filed under 35 USC §371 of PCT Application No. PCT/IL2012/000334, filing date Sep. 6, 2012, which claims priority to U.S. Provisional Application No. 61/573,120, filing date Sep. 7, 2011. Each of these applications is herein incorporated by reference in its entirety for all purposes.

FIELD OF THE INVENTION

The present invention relates to the field of ophthalmic measurement instruments, especially for use in performing tonometric and refractive measurements of the eye.

BACKGROUND OF THE INVENTION

In multifunction ophthalmic measurements, where each of the measurements has to be performed by a separate instrument, there arises the problem of how to mechanically arrange the instruments such that they can be simply switched from one to the other when changing the measurement to be performed. The optical axis of each measurement instrument must be accurately aligned with the eye to be measured, such that the problem in hand is not only the physical switching between one instrument and the other, but also the alignment of each instrument after it has been switched.

There exist a number of prior art documents which address this problem. For instance in U.S. Pat. No. 7,364,298, U.S. Pat. No. 7,515,321 and U.S. Pat. No. 7,771,050, all assigned to Nidek Co. Ltd., of Japan, there are described arrangements of ophthalmic apparatus capable of performing a plurality of eye characteristic measurements, using two separate measurement instruments stacked one on top of the other, which are moved in a vertical direction by a motion mechanism in order to switch measurements between them. Those patents relate to the combination of a tonometer for the measurement of intraocular pressure in a subject's eye using a unit blowing fluid onto the cornea through a nozzle, and an instrument for measuring the optical characteristics of the eye, in particular the eye's refractive power. In U.S. Pat. No. 7,909,462, assigned to Kabushiki Kaishi Topcon, there is described a similar combination instrument for tonometric and refractive characteristics measurements, in which the measurement heads are aligned side-by-side, and a method is described for switching between them by withdrawing them in a backward direction by a minimum distance, to enable the switch between them to be made in the minimum amount of time.

However, motion of complete measurement heads using linear motion stages can be a slow and mechanically complex technique. Furthermore, motion by means of a vertical lift when a lateral motion mechanism is also required to switch the measurement systems between the subject's left and right eyes may be equally complex. A simpler method of integrating two or more of such measurement modules into one instrument, which overcomes at least some of the disadvantages of prior art systems and methods, would therefore be advantageous.

The disclosures of each of the publications mentioned in this section and in other sections of the specification, are hereby incorporated by reference, each in its entirety.

SUMMARY

The present disclosure describes new exemplary systems for performing multiple function measurements on the eyes of the subject using separate ophthalmic measurement instruments, when it is required to perform the measurements sequentially by mechanically switching between them. In contrast to those prior art systems for this purpose, where the separate measurement instruments are stacked one on top of the other, and transfer between them is performed by mechanically moving the stacked instruments in a vertical direction on a lifting device, in the systems of the present disclosure, the separate measurement instruments are mounted on a base element which is rotatably pivoted around a joint at a location remote from the optical entry apertures of the instruments. When the base element is rotated around such a remote rotation axis, the optical entrance apertures of the separate measurement instruments pass the subject's eye sequentially. Thus a rotational motion around the pivoted joint is transformed into a linear motion at the eye of the subject. Such a rotational motion can be achieved by a mechanism substantially simpler, less costly and more compact than a linear lift mechanism, such as by the use of a stepping motor, or a worm drive, activated by means of an electric motor. A worm drive also has the advantage that it is generally mechanically self locking.

For performing vertical scans across the eye, the rotation may be achieved by means of a horizontal pivot axis, such that the tilt is vertically performed, whereas for a side-by-side configuration, such as is described in U.S. Pat. No. 7,909,462, the tilting motion can be implemented in a horizontal plane by means of a vertically aligned pivot axis. It is to be understood that any other plane of rotation may also be used, though vertical or horizontal tilting motion are the most practical. It is understood however, that although the disclosure is generally described in reference to the vertical tilt motion, it is understood to be applicable to any plane of tilt desired.

Additionally, another implementation of these systems incorporates a novel corneal thickness measurement arrangement, using the known Scheimpflug camera principle, in which the measurement head with the slit beam illuminator and the camera, is tilted as the scan proceeds across the subject's cornea, such that the illuminating slit beam always impinges on the cornea at normal incidence. This ensures that the strong corneal reflection cannot enter the camera and flood out the measurement, and also that any effects arising from oblique passage of the illuminating slit beam across the cornea are also eliminated.

There is therefore provided in accordance with one example implementation, an ophthalmic measurement system, comprising:
(i) a first optical measurement module having a first optical axis, measuring at least a first characteristic of a subject's eye,
(ii) a second optical measurement module having a second optical axis, measuring at least a second characteristic of a subject's eye, the second optical measurement module being vertically juxtaposed relative to the first optical measurement module, and
(iii) a base element to which the first and the second optical measurement modules are linked,
wherein the base element has a rotatable joint aligned such that angular rotation of the joint around its axis enables either of the first and the second optical measurement modules to be disposed in front of the subject's eye.

In such a system, the axis of the rotatable joint should generally be perpendicular to the first and second optical axes, and perpendicular to a line drawn between the first and second optical axes. The axis of the rotatable joint can be aligned generally horizontally or vertically, depending on the direction in which the measurement modules are to be switched in front of the subject's eye.

Furthermore, in any of the above-described systems, the first optical measurement module may be a tonometer, and the second optical measurement module may be a refractive power measurement system.

Additionally, the first and the second optical axes may be either parallel, or the first and second optical measurement modules may be aligned such that both the first and the second optical axes pass through the center of the rotatable joint axis.

In all of the above described systems, the axis of the rotatable joint should advantageously lie on a line generally parallel to the first and second optical axes, and between them.

Yet another example implementation involves an ophthalmic system for measurement of corneal thickness of an eye, comprising:
(i) a pivotally supported pachymetric measurement head comprising a source generating slit beam illumination and a Scheimpflug camera arranged at mutual angles, such that the camera images the passage of the slit beam through the cornea,
(ii) a scanning mechanism for traversing the pivotally supported measurement head across the eye in front of the cornea, and
(iii) a control system for rotating the pivotally supported measurement head in co-ordination with its scan position, such that the slit beam impinges generally normally on the cornea independently of the scan position of the measurement head.

In such an ophthalmic system, the scanning mechanism may comprise a linear motion stage traversing the eye, or a rotational motion platform pivoted at a point remote from the measurement head, for traversing the eye. The traversing across the eye may be performed in a plane having a horizontal or vertical angular orientation, or orientation in any other selected plane.

BRIEF DESCRIPTION OF THE DRAWINGS

The presently claimed invention will be understood and appreciated more fully from the following detailed description, taken in conjunction with the drawings in which:

DETAILED DESCRIPTION

Figure 1:
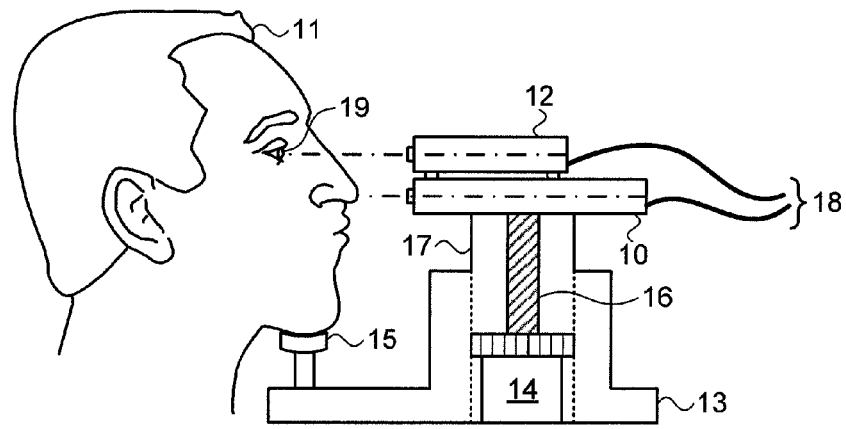
FIG. 1 illustrates schematically a prior art arrangement for switching between two measurement modules by means of a vertical motion system.

Reference is now made to FIG. 1, which illustrates schematically a prior art arrangement for switching between two measurement modules by means of a vertical motion system, such as one of those described in the above referenced patents—U.S. Pat. Nos. 7,364,298, 7,515,321 and 7,771,050. The two measurement modules could be an upper module 12, shown as a tonometric measurement instrument, with the measurement head optical aperture close to and aligned with the eye 19 of the subject 11 being measured, and a lower module 10, which could be a wavefront measurement instrument for measuring the optical characteristics of the eye. The optical axes of the two modules are also shown in FIG. 1. The wavefront measurement instrument could also be combined with other measurements which can conveniently be performed in the same module, such as corneal topography or corneal thickness measurements. The two measurement modules are mounted one of top of the other as a single unit, and are moved vertically in order to bring the optical axis of each measurement module to the level of the subject's eye 19. This motion may conveniently be accomplished by means of a sliding column 17, mounted within a base section 13, with the vertical motion provided by a nut and lead screw 16 mechanism, operated by an electric motor 14. Any other convenient form of vertical mechanical motion may also be used to move the slide 17 along its vertical axis, such as a scissor-jack mechanism. Cable bundles 18 exiting from the two measurement modules are used for providing the power supply for illumination sources within the measurement modules, and for transferring the measurement information back to the control system (not shown, but understood to be present in all of the systems shown in the application, both the prior art system of FIG. 1 and the exemplary systems shown in FIGS. 2A to 6B). In the above referenced prior art, the tonometer is in the upper position, possibly since it has to operate closer to the eye than the wavefront measurement system, and when the combination system is moved vertically upwards, the tonometer moves towards the forehead area of the subject which is generally more receded from position of the eye than the lower part of the face. However, any combination may be conveniently used.

Although the mechanical lift arrangement shown in FIG. 1 appears to be reasonably compact, since both of the instruments are shown to be of low height, if a corneal topographic measurement facility with a large radius Placido ring illumination system is built into the refractive characteristic measurements instrument, as described in PCT application No. PCT/IL2008/001148 to the assignee of the present application, then the required distance between the lower and upper instrument modules must be larger than that shown schematically in FIG. 1, leading to a larger range of motion required for the vertical lift assembly to move from one measurement axis to the other.

Figure 2A:
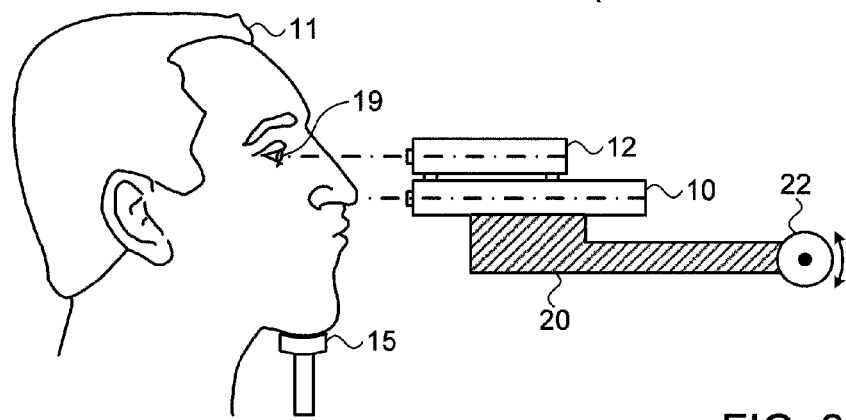
FIGS. 2A and 2B illustrate an exemplary schematic implementation of a system for switching between two ophthalmic measurement instruments by means of a rotational tilt, as shown in this disclosure, with each of the two drawings showing a different rotational alignment of the system.
Figure 2B:
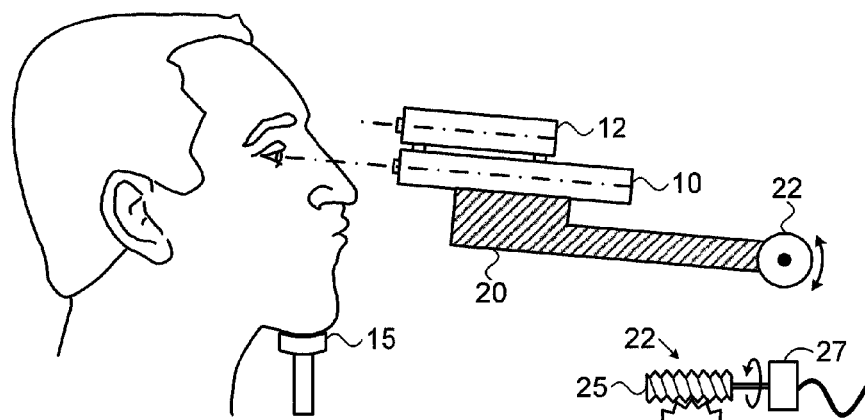
Figure 2C:
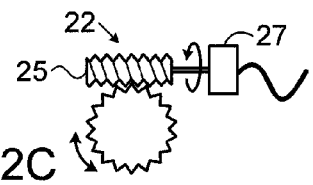
FIG. 2C shows one example of a drive system suitable for actuating the angular tilt required in the systems of FIGS. 2A and 2B.

Reference is now made to FIGS. 2A to 2C, which illustrate an exemplary implementation of a novel system for switching between two ophthalmic measurement modules, such as those shown in FIG. 1, without the need of the potentially complex prior art mechanical vertical lift mechanism shown in FIG. 1. FIGS. 2A and 2B show the two measurement modules mounted as previously shown in FIG. 1, one on top of the other, but instead of the base being moved vertically to switch between one and the other, the base element 20 is equipped at a position remote from the measurement module optical entrance apertures, with a remote rotary tilt joint 22, which can perform limited rotation. One exemplary method by which this rotary joint can be actuated is shown in FIG. 2C. By means of this rotation, the optical aperture of either of the measurement modules can be brought opposite the subject's eye 19. In the situation shown in FIG. 2A, the base is aligned such that the upper measurement module 12, in this example a tonometer, is aligned with its axis opposite the eye 19 of the subject 11. In the situation shown in FIG. 2B, the rotary tilt joint has been rotated until the system base is aligned such that the lower measurement module 12, in this case for a measurement of the refractive characteristics of the eye, is aligned with its axis opposite the eye 19 of the subject 11. It is noted that the eye of each subject is in a fixed vertical position relative to the chin mount 15, though the eye level of different subjects may be at different heights. Adjustment of the height of the chin support can then be used to align the eye at the same measurement reference height for each subject, as best as can be done by manual adjustment. The exact height adjustment can then be achieved by a fine adjustment of the tilt angle while viewing an image of the eye, in order to center the pupil for the measurement in hand. This centering can be done automatically by using a feedback control system using image processing software to generate the feedback signal to command rotation of the angular tilt axis until the eye is centered in the image. Thus, this tilt motion is used to replace any linear motion fine adjustment for centering the pupil for any measurement.

In FIGS. 2A and 2B, the base of the complete system is not shown in order to show more clearly the way in which the tiltable base element of the measurement modules can operate, but it is to be understood that the chin support 15 and the rotary tilt joint 22 and its drive system may both be mounted on a rigid baseplate for the entire system. A detailed description of an exemplary drive system for the rotary tilt joint 22 as shown in FIG. 2C, is given hereinbelow.

It is observed that in the exemplary alignment shown in FIG. 2B, the axis of the wavefront measurement instrument does not meet the eye normally, and it could be suspected that this may be a disadvantage of the present system compared with the prior art linear motion systems. However, since the subject can roll his/her eye, such an eye rotation action would ensure that the axis of the eye is parallel to the axis of the measurement module. For small angles of rotation of the eye, this effect is done automatically by the eye, so that objects are viewed optimally. This is particularly so since the refractive characteristic measurement module can include a fixation target, in order to control the patient fixation and to eliminate accommodation. It can also be used to enable an accommodation measurement. However any suitable object, preferably imaged at infinity, can be used in either of the instrument modules to ensure that the subject rolls the eye being measured to align its axis with that of each measurement module.

A further problem which arises with the exemplary embodiments shown in FIGS. 2A and 2B is related to the arc traced by the optical input aperture of each instrument, because of the offset location of the rotary joint 22 relative to the axes of the measurement modules. Thus, if the tonometer is correctly distanced from the subject's eye, as in FIG. 2A, then rotation of the base element 20 to align the lower refractive measurement instrument with the eye, as in FIG. 2B, will result in an increase in the distance of the entrance aperture from the subject's eye, such that the entrance aperture may not be at the correct working distance from the subject's eye. This can be compensated for by a predetermined longitudinal adjustment of the position of the two measurement instruments such that they are in the approximately correct focus position for the changed tilt angle, followed by a fine focusing action of the measurement module involved in order to reach a more exact imaging position. A feedback mechanism can be provided which adjusts the focal position of the input lens of the measurement instrument, according to an algorithm which ties the focal position to the angular orientation of the base, such that the measurement instrument is always at its correct working distance regardless of the angle at which the base is aligned.

Figure 3:
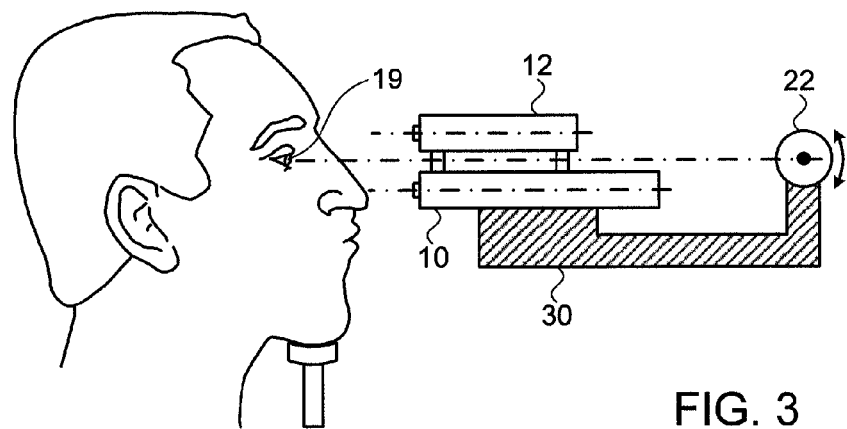
FIG. 3 illustrates schematically another implementation of the system of FIGS. 2A and 2B, but in which the rotational pivot joint is located on a center line equidistant from the optical axes of the two measurement instrument modules.
Figure 4:
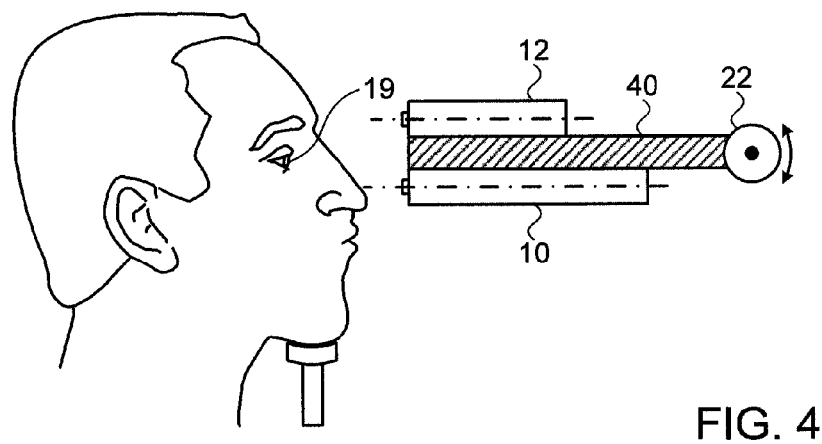
FIG. 4 illustrates schematically another implementation of the system of FIG. 3, using a base element situated between the two measurement modules.

An alternative and simpler solution which assists in reducing the problem of the dependence of focal distance with angular displacement is to arrange the rotational pivot joint to be located on a center line equidistant from the optical axes of the two measurement instrument modules. Such an implementation is shown in FIG. 3, where the base element 30 is provided with a bracket to ensure that the center of rotation of the rotary tilt joint 22 is equidistant from the two optical axes of the measurement instrument modules. FIG. 3 shows the measurement modules in the intermediate position, to show that the rotatable tilt joint 22 is aligned level with the subject's eye 19, and on the center line between the optical axes of the two measurement modules 10, 12. When making the two respective measurements, the base 30 will be tilted in either direction to align the optical entrance apertures of the respective instrument modules opposite the subject's eye 19. Alternatively, and perhaps more simply, the base element could be disposed between the two instruments, as shown in FIG. 4, such that it is naturally equidistant from the two optical axes. In either of these cases, rotation of the system is symmetrical about the center line between the optical axes of the two measurement modules, such that the need for focal length compensation to maintain each instrument at its correct working distance is minimized. However, patient movement will still necessitate active focus adjustment, such that the implementations suggested here merely reduce the level of refocus required because of the effect of the tilt mechanism.

Figure 5:
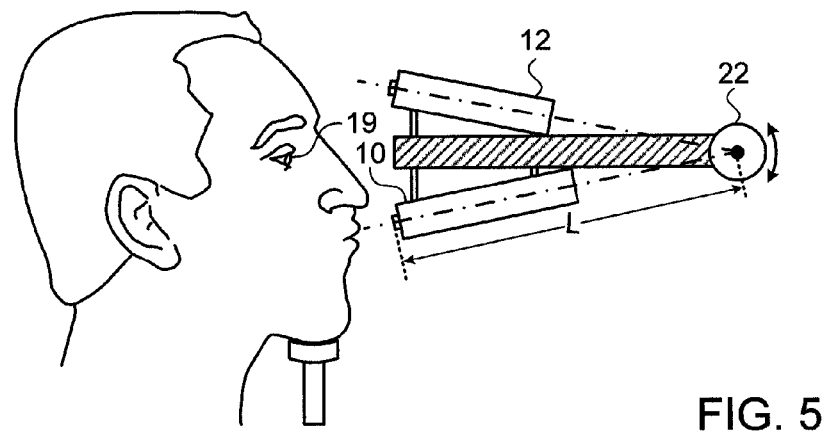
FIG. 5 illustrates schematically a further implementation of the systems of FIGS. 3 and 4, in which the two measurement modules are attached to the base element with each aligned so that the optical axis of each passes through the axis of rotation at the rotary pivot joint.

However, even in the implementations of FIGS. 3 and 4, when each measurement module is aligned opposite the eye of the subject, there is still need for the subject to implement an eye rotation in order to align the optical axis of the eye with the optical axis of the measurement module. Reference is now made to FIG. 5, which illustrates schematically an implementation which avoids these effects. In FIG. 5, the two measurement modules 10, 12 are not attached to the base element with their optical axes parallel, but rather with each aligned so that the optical axis of each passes through the axis of rotation at the rotary pivot joint 22. In such a situation, the optical axis of the instrument will always be aligned with the optical axis of the eye under test, regardless of the angle of alignment of the system and the height of the eye, and without the need of the subject to roll his eye to the axis of the measurement module in use at that point of time.

Any of the above described systems using rotary tilt joint motion provides these systems with a number of advantages over the prior art linear motion systems. In the first place a small rotary motion of the rotary tilt joint 22 can provide a significant controlled essentially linear movement of the measurement module's entrance aperture at the subject's eye, the relationship between the angular rotation and the lateral motion depending on the distance L between the tilt axis and the apertures of the measurement modules, as marked in FIG. 5 but as relevant in all of the implementations. Therefore, even measurement instruments having a large height and therefore spaced at an appropriately large distance from each other, can be used with a simple rotary joint implementation as described herewithin. An advantage of such a rotary tilt system is its compactness and simplicity in comparison to the prior art linear lift systems. Therefore, in order to achieve optimum size advantage, the distance L should be kept as small as possible to keep the instrument as compact as possible.

Secondly, rotary motion to a rotary axis may be significantly simpler to provide than the linear motion mechanisms of the prior art systems. Reference is now made back to FIG. 2C, which shows schematically an exemplary implementation in which the rotary motion is provided by means of a worm drive, with the worm gear 26 being attached to the axis of rotation of the rotary tilt joint, and the worm 25 being controllably driven by an electric motor 27, which could advantageously be a stepping motor. Such a worm drive has the advantage that the gear ratio is generally high, being equal to the "number of teeth on the worm gear-to-1" for a single start worm. Since only a small rotation is required, typically of a few degrees, and the drive motor may have a high rotational speed, such a high gear ratio is advantageous for this application. Furthermore, because of the weight of the combination measurement system including the two measurement modules and their base, a significant torque may be required in order to change its angular orientation, especially to raise the entire system. Therefore, such a worm drive with a high gear ratio also assists in converting the comparatively low torque of the drive motor to a torque suitable for angularly raising the combination measurement system. Finally, since such a worm drive is generally a one-way drive, from the worm to the worm gear (provided, usually, that the tangent of the worm lead angle is less than the coefficient of friction between the drive surfaces), the system is self locking with respect to torque applied from the worm gear, and the weight of the combination measurement system will not generally be able to rotate the rotary tilt joint. However it is to be understood that use of a worm drive is not the only method of providing rotation about an axis, and that this illustrated example is not meant to limit the possible methods of implementing such rotary motion. A directly coupled stepping motor could also be used, or a motor driving a spur gear train, or any other suitable drive mechanism providing controlled angular rotation motion. In any event, any such rotary motion provider is generally simpler and of lower cost than a linear motion system.

The advantages of the use of a rotary tilt joint in maintaining optimum compactness of the system have already been mentioned hereinabove. The reduction in the overall level of motion required by the system, especially with respect to the rear end of the measurement modules at which the operating cables are attached, is significant in maintaining compactness of the system. In addition, the significant reduction of lateral motion at the rear end of the measurement modules results in almost complete elimination of lateral motion of the cable bundle, and hence longer life time and higher reliability. In prior art systems, the cables may be subject to chafing by the constant vertical motion between the two measurement modules. However, the left to right motion in order to switch between the subject's eyes will still need to be maintained and its effect on the cable bundle will therefore not be canceled.

The use of the rotary tilt joint in the above described systems essentially replaces the linear motion along one axis by an angular motion which simulates the linear motion for small angular displacements. This effect can be used in order to simplify the scanning operation required when performing a pachymetric measurement over the entire profile of the cornea of the eye using a Scheimpflug method. However, it is to be emphasized that the measurement technique described can also be performed using direct linear motion of the measurement head, such that it is not limited to use of the tilting configurations of the present disclosure.

Figure 6A:
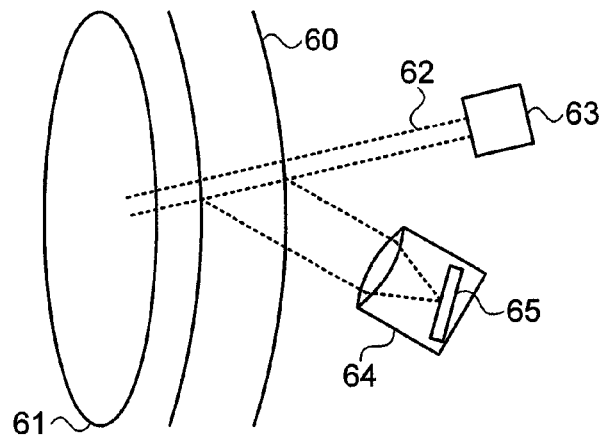
FIGS. 6A and 6B illustrate a novel goniometric method, which can use the tilting technique of the present disclosure, in order to simplify a scanning pachymetric measurement over the entire profile of the cornea of the eye.
Figure 6B:
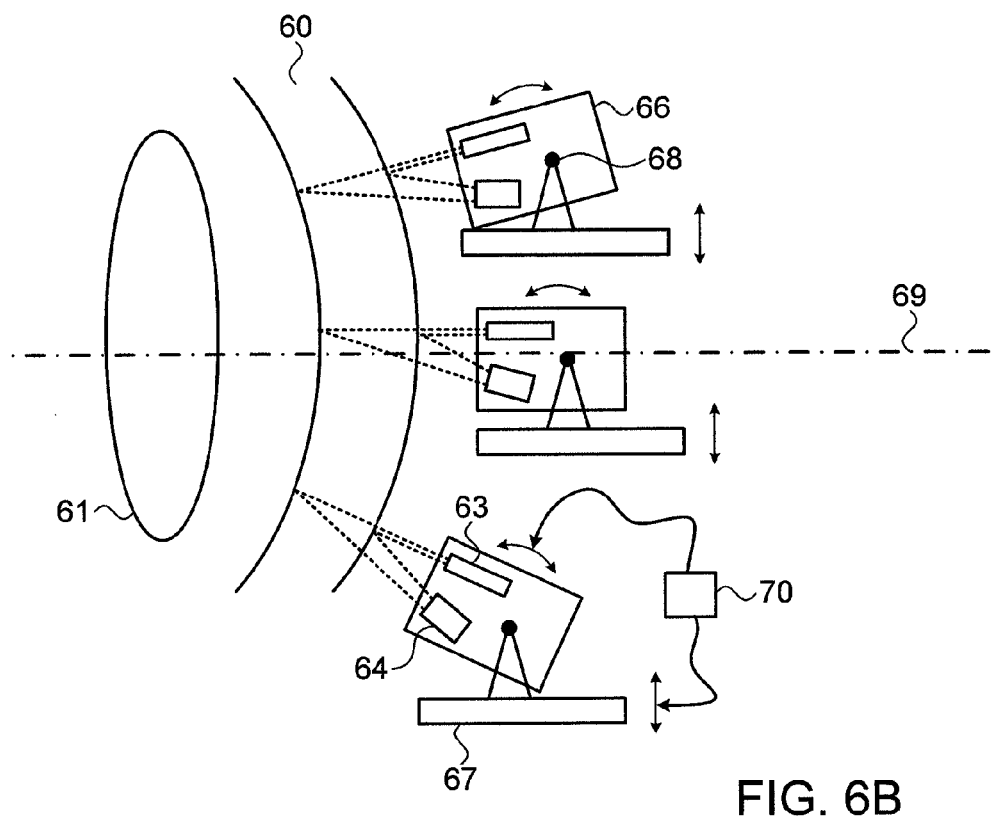

Reference is now made to FIGS. 6A and 6B to illustrate this application. In FIG. 6A, there is shown schematically an exemplary optical arrangement for measurement of the thickness of the cornea 60, by illuminating it with an incident slit beam 62 derived from an illumination source 63, generally using blue light such as a LED source with a central wavelength of 450 nm. The lens 61 is shown behind the cornea. The light scattered by the cornea is imaged by the camera 64, and the image information, in particular the length of the slit light scattered by the cornea in its path through the cornea, provides an indication of the corneal thickness. In order to ensure accurate imaging methods, and in particular, accurate measurements of the slit image length, the Scheimpflug principle is used with a tilted camera plane 65 in order to ensure that the image of the slit lamp beam is focused across the entire thickness of the cornea. In order to perform such a pachymetric measurement over the entire surface of the cornea, prior art measurements, such as those described in U.S. Pat. No. 6,286, 958 to G. Koest et al for "Device for the Examination of an Eye using a Scheimpflug Camera and a Slit Light Projector for Photographing Slit Images of an Eye", have used a rotating slit lamp and camera arrangement. However, this is a mechanically complex solution. Another solution is presented in U.S. Pat. No. 5,512,965 to R. K. Snook for "Ophthalmic Instrument and Method of making Ophthalmic Determinations using Scheimpflug Corrections", where the slit itself is scanned across the corneal area. This solution however suffers from a change in the imaged width of the cornea at different points in the scan due to imaging through different thicknesses of the cornea. If, on the other hand, in order to simplify the technique, a simple linear scan across the cornea is performed, whether by means of a linear motion stage or by means of the tilt mechanism described in this application, because of the different path lengths of the light through the cornea at different lateral points on the eye, the geometry of the measurement becomes complex, since the reflected image is determined both by the corneal thickness which it is desired to measure, and by the different path lengths of the light resulting from the oblique passages of the probe beam through the cornea, as a result of which, the image becomes partially smeared out. For a small part of the scan in the method used in U.S. Pat. No. 5,512,965, the strong reflection of the input beam from the corneal surface will be at such an angle that it will enter the camera thus rendering some of the scanned images unfit for analysis.

In order to avoid this complication, it is necessary to ensure that the slit beam illumination always enters the eye normal to the anterior corneal surface, so that the strong corneal reflection cannot enter the camera. This is shown in FIG. 6B, for several different positions of the incident light beam 62 across the corneal surface. Such a normal incidence scan can be achieved by means of a combination of a linear scan and a rotation of the measurement head such that it always is directed approximately normal to the corneal surface as it scans across the cornea. The base of the measurement head 67 is moved linearly across the height of the eye, as indicated by the vertical double-headed arrows, while the measurement head itself 66, containing the slit beam source 63 and the imaging camera 64, is rotated on a pivot 68, as indicated by the curved arc double-headed arrows, such that the pachymetric imaging measurement is always performed normal to the corneal surface. The rotation is synchronized with the position of the scan relative to the optical axis 69 of the eye and the distance from the eye, to ensure that the correct tilt is obtained at each scanning point. This can be achieved by means of a control system 70 linking the two motions, the control link being schematically shown in FIG. 6B by the connecting arrows to the two motions to be co-ordinated, but being understood to include the elements needed to link the motions in the desired way—such as sensors or encoders to determine the position of the two motions, motion systems such as stepping motors to perform the motion, and the control circuits themselves to maintain the correct relation between the linear and rotational positions. This control system could be part of the main control system for operating the complete instrument.

This description assumes that the scanning motion is performed across the height of the eye, but it is to be understood that the scan can also be performed laterally across the width of the eye, in which case, the measurement head rotation has to be performed around a vertical pivot axis. As previously mentioned, the linear scan can be performed by any method, whether by means of a linear motion stage or by means of the tilt mechanism described in this application, or be another scanning mechanism which provides the necessary motion of the beam across the eye.

Although the combination of ophthalmic measurement instruments described in this disclosure is a commonly used combination, different combinations are also possible, and this disclosure is not intended to be limited by this particular combination of a tonometer, with a wavefront measurement instrument for characterizing refractive properties of the eye, with or without measurement of the topography and thickness of the cornea.

It is appreciated by persons skilled in the art that the present invention is not limited by what has been particularly shown and described hereinabove. Rather the scope of the present invention includes both combinations and subcombinations of various features described hereinabove as well as variations and modifications thereto which would occur to a person of skill in the art upon reading the above description and which are not in the prior art.

What is claimed is:

1. An ophthalmic measurement system, comprising:
    a first optical measurement module having a first optical axis, measuring at least a first characteristic of a subject's eye;
    a second optical measurement module having a second optical axis, measuring at least a second characteristic of a subject's eye, said second optical measurement module being juxtaposed relative to said first optical measurement module; and
    a base element to which said first and said second optical measurement modules are linked,
    wherein said base element has a rotatable pivot joint aligned such that angular rotation of said pivot joint around its axis rotates said base such that either of said first and said second optical measurement modules is rotated into a position in front of said subject's eye.

2. An ophthalmic measurement system according to claim 1, wherein said axis of said rotatable joint is generally perpendicular to said first and second optical axes, and perpendicular to a line drawn between said first and second optical axes.

3. An ophthalmic measurement system according to claim 1, wherein said rotatable joint has its axis aligned generally horizontally.

4. An ophthalmic measurement system according to claim 1, wherein said rotatable joint has its axis aligned generally vertically.

5. An ophthalmic measurement system according to claim 1, wherein said first optical measurement module is a tonometer.

6. An ophthalmic measurement system according to claim 1 wherein said second optical measurement module is a refractive power measurement system.

7. An ophthalmic measurement system according claim 1, wherein said first and said second optical axes are parallel.

8. An ophthalmic measurement system according to claim 1, wherein said first and second optical measurement modules aligned are such that both said first and said second optical axes pass through said center of said rotatable joint axis.

9. An ophthalmic measurement system according to claim 1, wherein said axis of said rotatable joint lies on a line generally parallel to said first and second optical axes, and between them.

10. An ophthalmic system for measurement of corneal thickness of an eye, comprising:
    a pivotally supported pachymetric measurement head comprising a source generating slit beam illumination and a Scheimpflug camera arranged at mutual angles, such that the camera images the passage of the slit beam through the cornea;
    a scanning mechanism for traversing said pivotally supported measurement head across the eye in front of the cornea; and
    a control system for rotating said pivotally supported measurement head in co-ordination with its scan position, such that said slit beam impinges generally normally on said cornea independently of the scan position of said measurement head.

11. An ophthalmic system according to claim 10, wherein said scanning mechanism comprises a linear motion stage traversing the eye.

12. An ophthalmic system according to claim 10, wherein said scanning mechanism comprises a rotational motion platform pivoted at a point remote from said measurement head, for traversing the eye.

13. An ophthalmic system according to claim 10, wherein said traversing across the eye is performed in a plane having a horizontal or vertical angular orientation.

14. An ophthalmic system according to claim 10, wherein said traversing across the eye is performed in a plane having an angular orientation other than horizontal or vertical.

* * * * *